United States Patent
Robert et al.

(10) Patent No.: US 7,920,250 B2
(45) Date of Patent: Apr. 5, 2011

(54) SYSTEM FOR THE DETECTION BY A MOTOR VEHICLE OF A PHENOMENON THAT INTERFERES WITH VISIBILITY

(75) Inventors: Caroline Robert, Paris (FR); Joël Leleve, Epinay sur Seine (FR); David Hue, Chatou (FR)

(73) Assignee: Valeo Vision, Bobigny (FR)

(*) Notice: Subject to any disclaimer, the term of this patent is extended or adjusted under 35 U.S.C. 154(b) by 152 days.

(21) Appl. No.: 12/181,585

(22) Filed: Jul. 29, 2008

(65) Prior Publication Data

US 2009/0046894 A1    Feb. 19, 2009

(30) Foreign Application Priority Data

Aug. 3, 2007 (FR) .................................. 07 05715

(51) Int. Cl.
 *G01B 3/36* (2006.01)
(52) U.S. Cl. ........................................ 356/28; 356/28.5
(58) Field of Classification Search ................ 356/28
 See application file for complete search history.

(56) References Cited

U.S. PATENT DOCUMENTS

| | | | |
|---|---|---|---|
| 6,803,574 | B2 | 10/2004 | Abel et al. |
| 7,350,945 | B2 | 4/2008 | Albou et al. |
| 2003/0066965 | A1 | 4/2003 | Abel et al. |
| 2004/0218401 | A1* | 11/2004 | Okubo et al. ............... 362/526 |
| 2005/0180149 | A1 | 8/2005 | Albou et al. |
| 2007/0031006 | A1 | 2/2007 | Leleve et al. |
| 2008/0140318 | A1* | 6/2008 | Breed ............................ 702/3 |

FOREIGN PATENT DOCUMENTS

| | | |
|---|---|---|
| EP | 1298481 A2 | 4/2003 |
| EP | 1498721 A1 | 1/2005 |
| EP | 1553429 A1 | 7/2005 |
| EP | 1715456 A1 | 10/2006 |
| EP | 1790541 A2 | 5/2007 |
| FR | 2847367 A1 | 5/2004 |

OTHER PUBLICATIONS

Leleve, J. et al.: "Fog Lamp Automation With Visibility Sensor: The Next Step of Lighting Automation," VDI Berichte, Dusseldorf, DE, No. 1907, 2005, pp. 151-160, ISSN: 0083-5560.
Reilhac, Patrice et al.: "OptiVeo: A Vision-Based Platform for Driving Assistance," SAE World Congress, XX, XX, 2006, pp. 229-235.

* cited by examiner

*Primary Examiner* — Thomas H Tarcza
*Assistant Examiner* — Luke D Ratcliffe
(74) *Attorney, Agent, or Firm* — Jacox, Meckstroth & Jenkins

(57) ABSTRACT

A process for the detection from a vehicle of a visibility interference phenomenon, comprising the following steps: the emission of a beam of light to illuminate the rear of the vehicle, the beam of light being emitted into a field of vision of a camera mounted in the vehicle, and the determination of a presence and the nature of a visibility interference phenomenon on the basis of at least one image captured by the camera.

13 Claims, 6 Drawing Sheets

SYSTEM FOR THE DETECTION BY A MOTOR VEHICLE OF A PHENOMENON THAT INTERFERES WITH VISIBILITY

CROSS-REFERENCE TO RELATED APPLICATIONS

This application claims priority to French Application No. 0705715 filed Aug. 3, 2007, which application is incorporated herein by reference and made a part hereof.

BACKGROUND OF THE INVENTION

1. Field of the Invention

The present invention relates to a process for detecting a phenomenon that interferes with visibility and a detection device allowing this process to be implemented.

It will be used in particular in the sphere of motor vehicles.

2. Description of the Related Art

In the case of motor vehicle applications, processes are already known under the state of the art, whereby the presence of a solid obstacle such as a vehicle following closely behind can be observed and a warning can be given if this vehicle gets too close. Such systems work for example on the basis of a distance sensor. In the event of such an obstacle being present and provided that the rear lights are switched on, on a wet road (regardless of whether it is actually raining or not), the visibility of the lights can be affected by a visibility interference such as spray of water produced by the rear wheels of the vehicle or the driver of the vehicle behind; this can be the cause of concern for the driver following and also for the driver being followed. However, such processes do not enable a visibility interference phenomenon to be detected.

Such detection devices are also known. For example, EP 1 715 456, which is equivalent to U.S. Patent Publication 2007/0031006, which is incorporated herein by reference and made a part hereof, describes a process for detecting evening fog along a road in front of a vehicle, comprising a system for illuminating the roadway with the vehicle's headlights. Such systems work on the basis of capturing a series of images of the roadway, extracting a halo of light from these images created by the headlights, comparing this with the nearest elliptical curve and deducing the presence or the absence of fog.

The document EP 1 498 721 describes a fog detection process, comprising a numerical camera, which scans the environment around the vehicle and an imaging system, which compares the luminosity of each pixel of the camera to a predetermined value and then deduces the presence of fog if the luminosity of any of the pixels is lower than the said predetermined value.

The document EP 1 298 481, which is equivalent to U.S. Pat. No. 6,803,574, which is incorporated herein by reference and made a part hereof, describes a night vision device, comprising an infra-red emitter, a detector and a display device. The emitter comprises one or more pulse emitting diodes, which are operated by a driver, which operates simultaneously the detector or a camera. This document does not cover fog applications.

The document EP 1 553 429, which is equivalent to U.S. Pat. No. 7,350,945, which is incorporated herein by reference and made a part hereof, describes a system for detecting traffic conditions on a roadway (both weather conditions and the detection of obstacles), which is mounted on a motor vehicle and comprises at least one light projector having a first light source emitting a visible beam of light and at least one source of modulatable light, in particular at a high frequency, emitting a beam of infra-red light along the road ahead and at least one camera able to capture images of the road ahead.

The document "Fog lamp automation with visibility sensor, the next step of lighting automation", by J. Lelevé et al., appearing in the VDI Report No. 1907, 2005, describes a passive fog detection system, based on cameras and image processing but without the emission of a light beam.

The document "OptiVeo: A Vision-Based Platform for Driving Assistance", by P. Reilhac et al., from the SAE World Congress, 2006, describes a passive fog detection system, on the basis of cameras and image processing, but not including the emission of a light beam.

The document EP 1 790 541, which is equivalent to U.S. Patent Publication 2007/01153357, which is incorporated herein by reference and made a part hereof, describes a device for detecting dirty marks on the windscreen of a motor vehicle, which uses two cameras and an image processing system.

The document FR 2 847 367 describes a passive process and device to determine the distance visibility in the present of an element interfering with visibility such as fog, although this does not comprise any emission of a light beam.

SUMMARY OF THE INVENTION

An object of the present invention is to provide means of detecting a phenomenon that interferes with visibility.

According to an initial embodiment, this object is achieved by a process that enables a phenomenon interfering with visibility to be detected and comprises the following stages:
  the emission of a beam of light from a vehicle, this beam being emitted from a motor vehicle within the field of vision of a camera mounted in the vehicle, and
  the determination of the presence and the nature of the phenomenon that interferes with visibility on the basis of at least one image captured by the camera.

As will be seen in detail below, such a process has the advantage of analysing such a phenomenon by means of an image captured by a video camera. No complex electronic gadgetry is required. Moreover, the use of a video camera is not very costly.

According to other non-limitative embodiments, the process also has the following characteristics:
  the nature of the phenomenon interfering with visibility is calculated on the basis of the homogeneity and the granulometry of the phenomenon on the image. These two criteria can show whether the phenomenon is, for example, fog or a spray of water;
  the calculation of the nature of the phenomenon is made on the basis of a tracking movement of the phenomenon. This enables a precise distinction to be made between fog and a spray of water;
  the beam of light is modulated. This permits the use of a multi-function camera which can be used to detect the presence of such a phenomenon and another function such as a parking aid.

According to a second embodiment, the invention concerns a device for the detection of a phenomenon interfering with visibility, comprising:
  a light source emitting a beam of light from a vehicle, with this light beam being emitted within the field of vision of a camera mounted in the vehicle; and
  a control unit to determine the presence and the nature of such a phenomenon on the basis of at least one image captured by the camera.

According to a third embodiment, the invention concerns a computer programming product having one or more sequences of commands that can be carried out by a data processing unit, the execution of the sequences setting in motion the process in accordance with any of the above characteristics.

These and other objects and advantages of the invention will be apparent from the following description, the accompanying drawings and the appended claims.

BRIEF DESCRIPTION OF THE ACCOMPANYING DRAWINGS

Other characteristics and advantages of the present invention will be best understood from the description and the non-limitative figures including the following:

DETAILED DESCRIPTION OF THE PREFERRED EMBODIMENTS

On a wet road, either as a result of wet weather or of fog, visibility of the rear lights of a motor vehicle (car, lorry etc.) for a driver in a following vehicle may be affected by a phenomenon that interferes with the visibility of another motor vehicle driver in the form, for example, of a spray of water thrown up from behind the vehicle. It is therefore interesting to assess the presence and the nature of this phenomenon that interferes with visibility so that, if necessary, the vehicle's lighting and signalling systems can be switched on and/or increased (lights/headlights) so that the driver of the car behind can distinguish more easily the signals of the vehicle in front.

Figure 1:
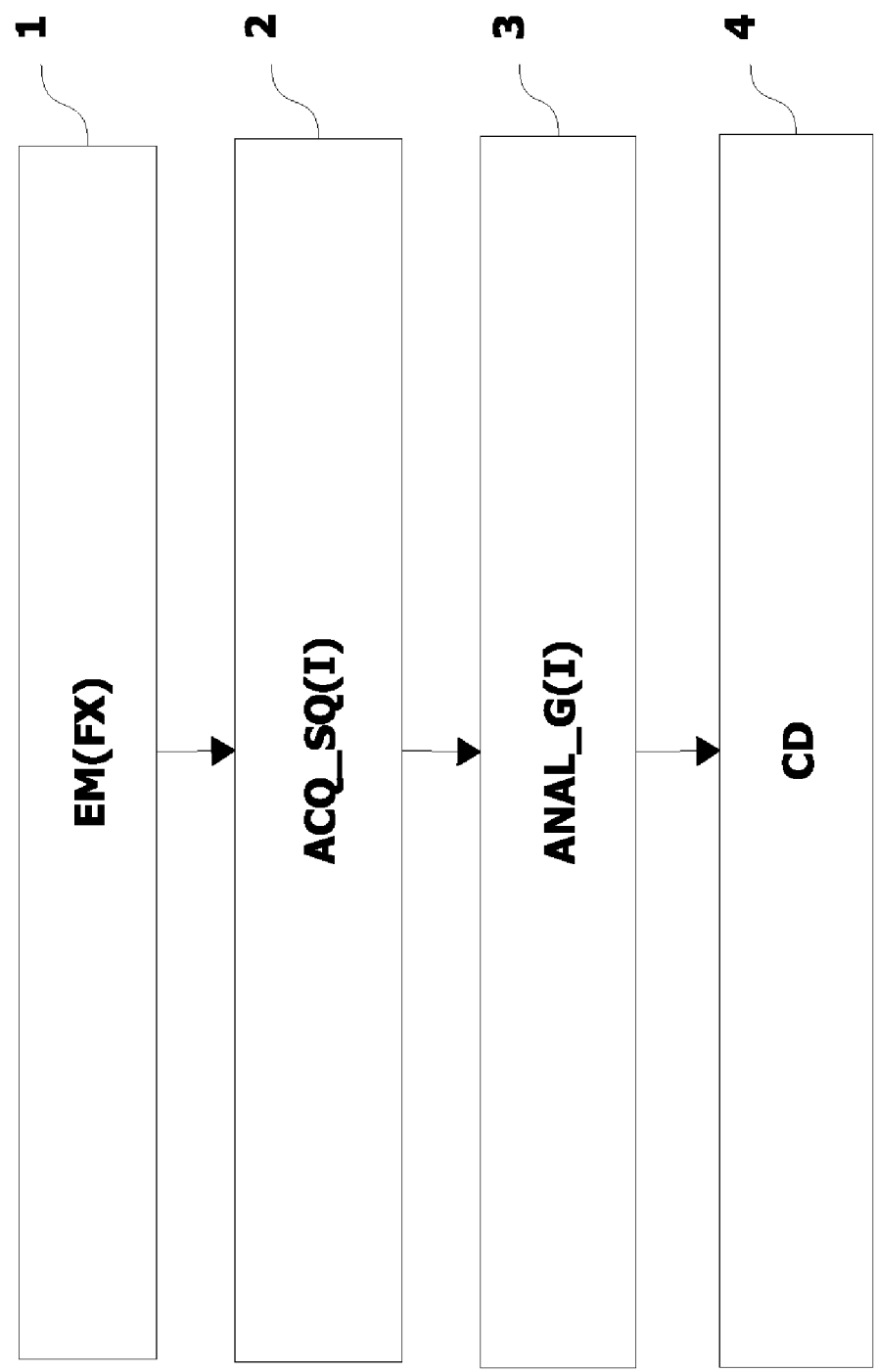
FIG. 1 represents a diagram of a non-limitative embodiment of the detection process in accordance with the invention.

The process of detecting such a phenomenon in accordance with the invention allows such a form of detection and is described in a non-limitative embodiment in FIG. 1.

In this application, the detection is carried out using a detection device mounted in a vehicle V comprising a video camera, described in detail below.

The detection process comprises the following stages as illustrated in FIG. 1:
  the emission of a beam of light FX from a vehicle V, this beam of light being emitted within the field of vision of the camera CAM of the vehicle V (stage EM(FX) or block 1 in FIG. 1), and
  the determination of the presence and the nature of an interference phenomenon G on the basis of at least one image I captured by the camera CAM (stage ANAL_G (I) block 3 in FIG. 1).
It also comprises the following stage:
  the capture of an image I by the camera CAM (stage ACQ_SQ(I) or block 2 in FIG. 1).

A detailed description of these stages follows:

In the first stage 1), a beam of light FX is emitted from the vehicle V, this beam of light being emitted within the field of vision of the camera CAM of the vehicle V.

In one non-limitative embodiment of the invention, the beam of light FX is a beam of infra-red light with a wavelength of around 850 nm. This prevents the creation of any undesirable lighting effects on the rear of the vehicle in the presence of an interference phenomenon G and thereby prevents discomfort on the part of the drivers behind. Moreover, it ensures compatibility with the spectrum of detection of the camera CAM as it will be seen from a greater distance.

Furthermore, in another non-limitative embodiment of the invention, the beam of light FX is narrow. In one non-limitative example it has an opening angle of 4°. This prevents any possible loss of power. It also produces a concentration of energy in the beam of light FX and promotes the detection of an interference phenomenon at much greater distances.

The beam of light FX is generated by a light source DIOD described below.

Figure 2:
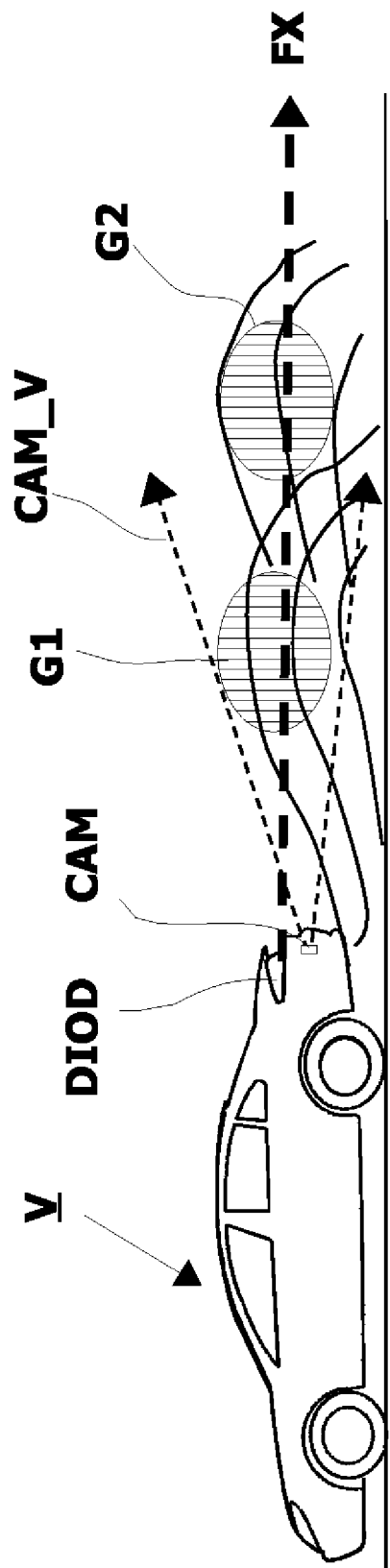
FIG. 2 is a schematic representation of a vehicle generating a phenomenon that interferes with visibility and has been detected by the process in accordance with FIG. 1.

FIG. 2 shows an example of a beam of light FX generated by a light source DIOD and emitted into the field of vision CAM_V of the camera CAM of the vehicle V. In the example shown, the beam of light FX is emitted behind the vehicle V. Moreover, two sprays of water G1 and G2 are shown and illuminated by the beam of light FX.

Figure 3:
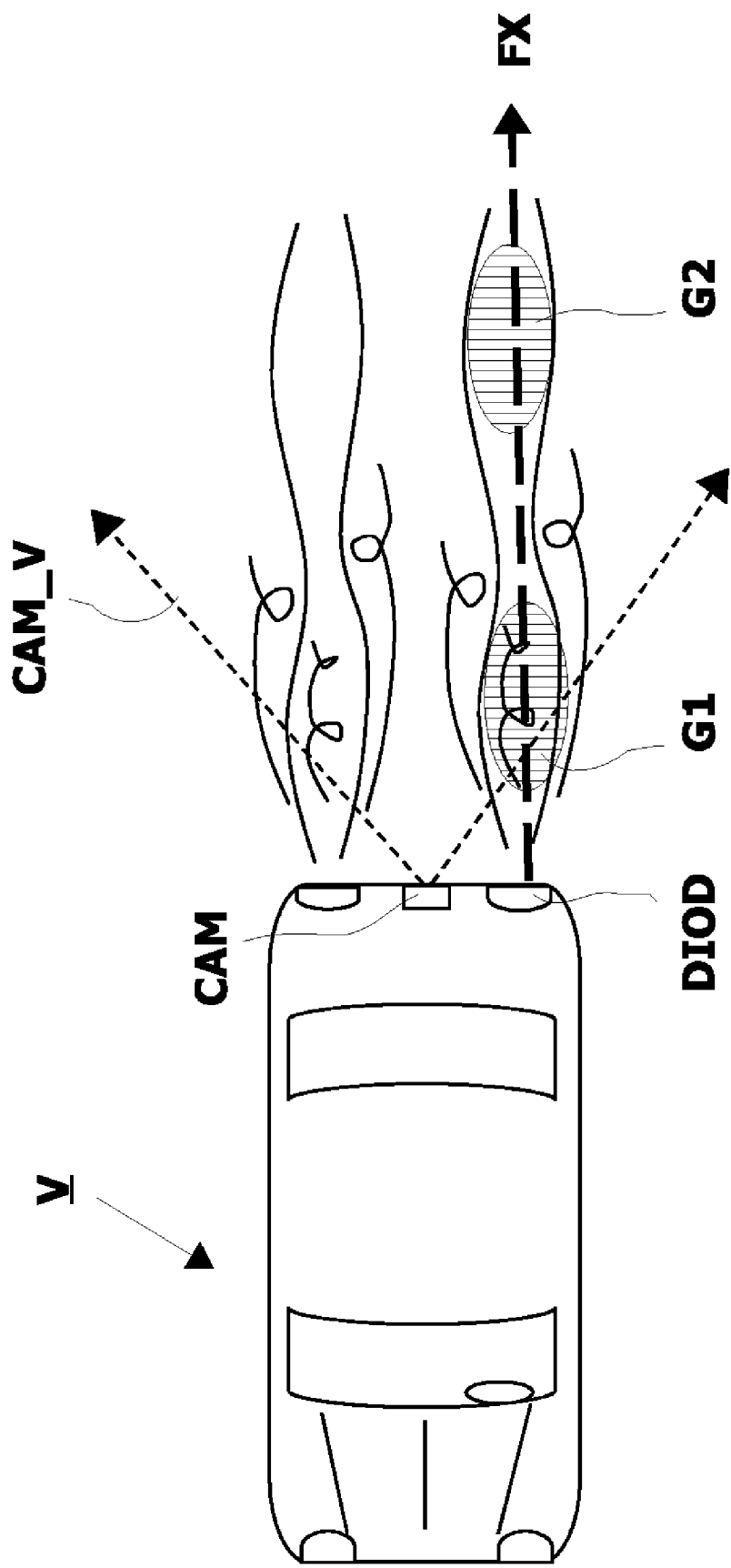
FIG. 3 is a plan view of FIG. 2.

FIG. 3 shows a plan view of FIG. 2. The position of the light source DIOD inside a rear light can be seen together with the position of the camera CAM between the two rear lights.

In one non-limitative embodiment of the invention, the generation of the beam of light FX is effected by activating the rear lights. This enables the driver to be sure of detecting an interference phenomenon such as a spray of water when it is raining or when the carriageway is wet and consequently to adapt the lighting of his rear lights in accordance with the nature of the interference phenomenon.

In a second stage 2), an image I is captured by the camera of the vehicle V.

As the video camera CAM is positioned, as shown, at the rear of the vehicle V, the captured image I represents the environment of the vehicle V within the field of the camera CAM and thus the rear of the vehicle V. In this way, an interference phenomenon G located at the rear of the vehicle V will be detected. In a non-limitative example, the camera CAM is positioned in the vicinity of one of the rear lights of the vehicle V.

In this way, the beam of light FX emitted from one of the rear lights is diffused through the particles of the interference phenomenon G in suspension in the atmosphere (after the movement of wheels along a wet carriageway, for example). As the wavelength of this beam of light is compatible with the analysis spectrum of the camera CAM, and as the particles constituting the interference phenomenon G located within the field of vision of the camera CAM, it is possible to capture an image that integrates the diffused light within the interference phenomenon G.

It will be noted that this stage, during which the images are captured, cannot be included in the process as described, but can be part of another process that is carried out in advance of the process described.

It will also be noted that the first and the second stages can be carried out in parallel.

In a third stage 3), the presence and the nature of a visibility interference phenomenon G can be determined on the basis of the image I captured by the camera CAM.

An analysis of this image I will enable:

the presence and the nature of the interference phenomenon (rain, fog) to be determined and thereby for the reduction of visibility of the rear signalling system or of the front lights to be deduced, so as to be able to compensate accordingly by increasing the intensity of the lights and the signals in question (in the example, where the beam illuminates the rear of the vehicle, the rear lights) or by activating the fog lights or by switching the headlights from a dipped beam to an undipped beam, and the presence of an obstacle O to be revealed, and in particular, the presence of a following vehicle so as to optimize the consumption of additional energy by the lights (and also to limit the effect of these actions on the service life of filament bulbs).

Figure 4:
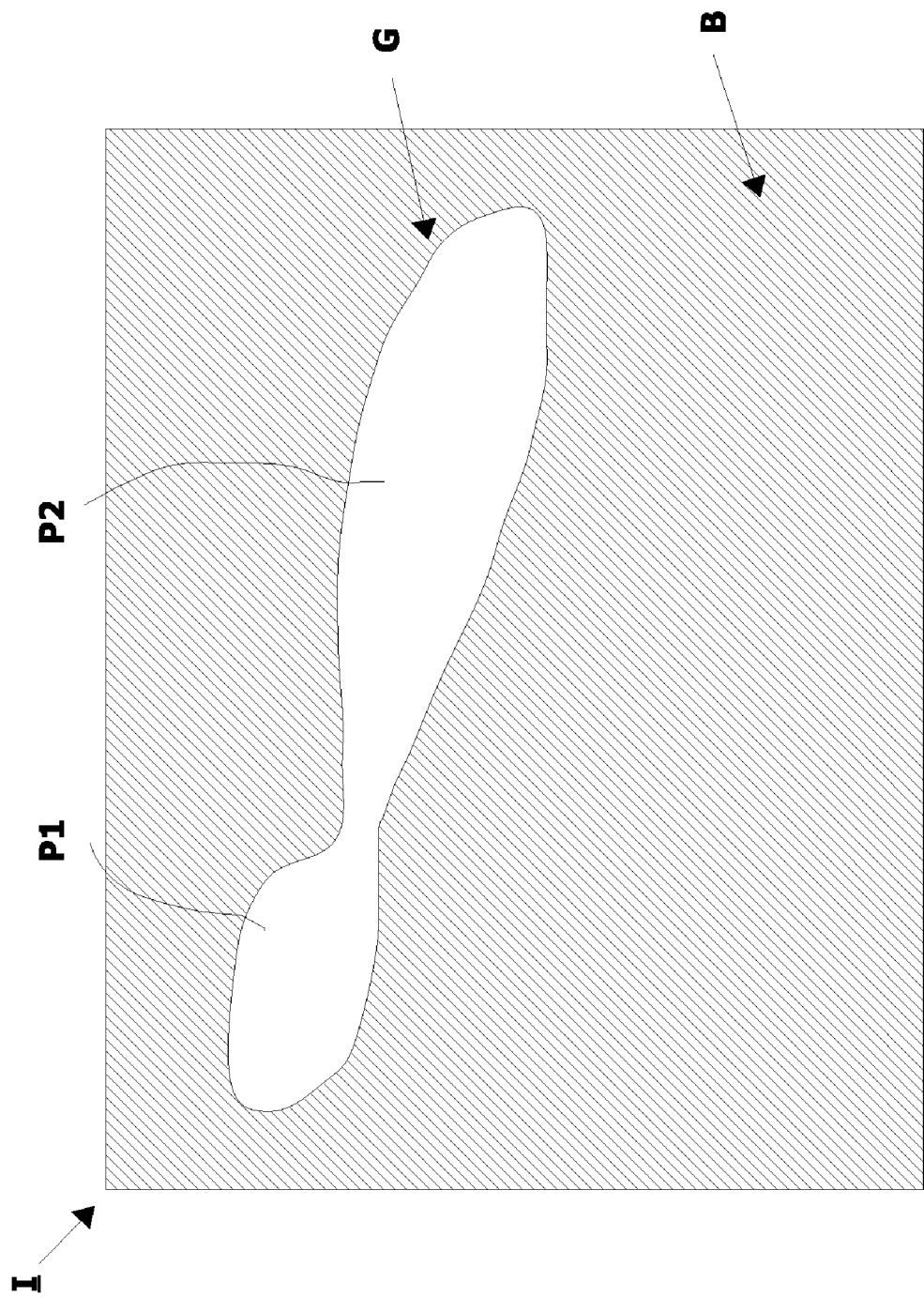
FIG. 4 is a first example of a captured image of a phenomenon interfering with visibility that has been detected by the process in FIG. 1.
Figure 5:
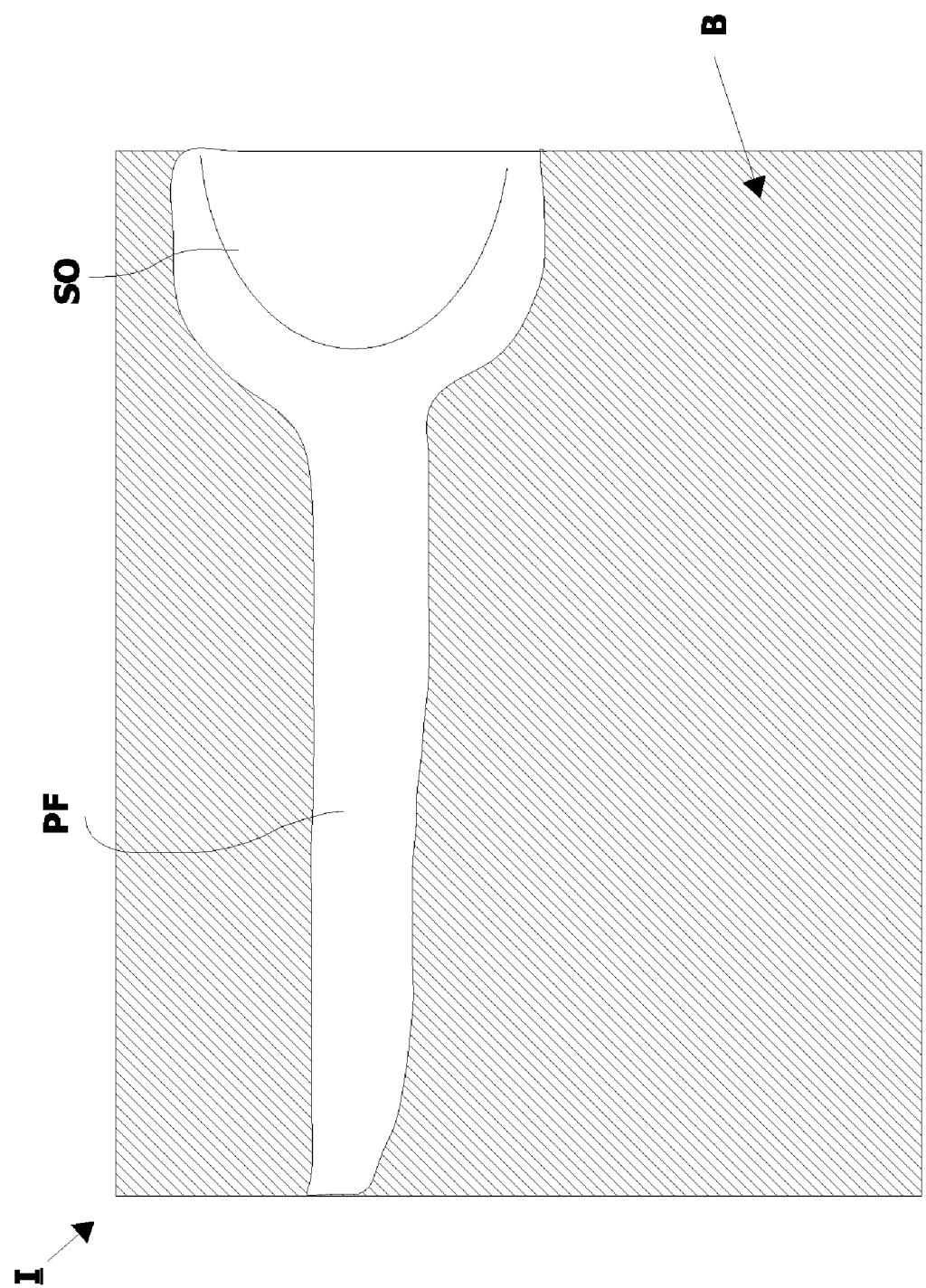
FIG. 5 is a second example of a captured image of a phenomenon interfering with visibility that has been detected by the process in FIG. 1.

Two non-limitative examples of an image I captured by the camera CAM are shown in FIGS. 4 and 5.

These images I give an indication of the diffused light during the night with a narrow beam of light FX. The beam is emitted from a light source DIOD situated on the left of the image I and above the camera CAM.

The white area represents the diffused night light with the beam of light FX, while the shaded area marked B represents the surrounding environment, here the rear, of the vehicle V within the field of vision of the camera CAM that is not illuminated by the beam of light FX.

The example in FIG. 4 shows the environment at the rear of the vehicle V in the presence of rain, without an obstacle O in the field of vision CAM_V of the camera CAM, with the image I revealing areas of water P1 and P2, indicating the presence of an interference phenomenon G, such as a spray of water produced by aerodynamic turbulence behind the vehicle V.

The example in FIG. 5 shows the environment behind the vehicle V in the presence of fog, with an obstacle O (for example, a following vehicle).

In the presence of fog PF, which is more homogenous and less moving than areas of water, the beam of light FX appears more continuous. On the same image, an external light source appears in the filed of vision, to the right of the image I. This could be an obstacle O, such as the headlight of a following vehicle, or alternatively a fixed light source in the countryside. The detection and characterization of this type of light source in the image is simple if tracking methods are used, based, for example, on the detection of shadows so as to pick out the contours of a following vehicle. As these methods are well known to the expert, they will not be described here.

In this way, using the images captured by the camera CAM, the following can be detected:

the presence and the nature of an obstacle O; and the presence and the nature of an interference phenomenon.

With regard to the detection of an obstacle O, the information on the presence of a following vehicle can be used to optimize the control of the intensity of the vehicle's signalling functions. In this way, it is possible to adjust the intensity of the rear lights depending on the presence or otherwise of a vehicle following closely behind (to prevent dazzling). This will have the effect of increasing safety for both drivers in question.

It will also be noted that, at the rear of the vehicle, the intensity of the rear side lights is characterized by a number of standard points. According to one European Standard (EEC R7), the intensity of these points varies between 0.05 cd and 4 cd minimum depending on the points. The maximum permitted is 12 cd for a single light and 17 cd for a set of lights.

In this way, if water is detected, the intensity of the lights can be increased, but if both water and the presence of a driver close behind are detected, the intensity of the lights can be increased accordingly (that is to say, less than would be the case in the absence of this vehicle so as to reduce the dazzle and less than in the presence of a more distant vehicle).

With regard to the detection of a visibility interference phenomenon G, the characterization of the nature of this phenomenon is based on the homogeneity and the granulometry of the diffused light. It is because of these two parameters that a distinction can be made between water and fog.

The advantage of being able to discriminate between water and fog has the effect of being able to activate a particular form of signalling in the presence of fog, that is to say, the use of the fog lights, or increasing the intensity of the rear lights in the event of a spray of water, for example.

It will be noted that in the case that there is a need to establish whether the phenomenon is a mixture of spray and rain, the additional use of a rain sensor is possible. This sensor can also confirm that the rainfall is regular.

The manner of determining the homogeneity of the diffused light is already known to experts. In a non-limitative example, it can be based on an analysis of the texture of an image I by using a probabilistic approach, such as co-occurrence matrices and more particularly its homogeneity criterion. As this method is well known to the expert, it will not be described any further here.

The determination of the granulometry (the attribute of the texture) of the diffused light is also known to the expert. In a non-limitative example, it can be based on an analysis of the texture of an image I by using probabilistic approaches, such as co-occurrence matrices and/or frequential approaches, the Fourier transform, breakdown into wavelets etc. As these methods are all known to the experts, they will not be described any further here.

In this way, if, on the captured image I, there is neither the interference phenomenon G nor an obstacle O to be seen, the beam of light FX will not be seen on the image. However, if, on the captured image I, there is no interference phenomenon G, but there is an obstacle O, to be seen this obstacle can easily be illuminated and characterized.

If, on the captured image I, an interference phenomenon G but no obstacle O is to be seen, the interference phenomenon is illuminated and visible.

If, on the captured image I, there is both an interference phenomenon G and an obstacle O to be seen, both the interference phenomenon G and the obstacle O will be illuminated and visible.

In the event of the presence of an interference phenomenon G, if, on the captured image I, the beam of light FX reveals non-homogenous zones for which the texture (indicated by the granulometry) is not smooth, it can be concluded that there are areas of water present (as for example in a wet carriageway with or without rain). At this moment, the intensity of the vehicle's lights can be increased.

If, on the captured image I, the beam of light FX reveals a continuous homogenous zone for which the texture (indicated by the granulometry) is smoother, it can be concluded that fog is present (unless it is fine rain that is present without the formation of spray). At this moment, the fog lights can be switched on.

In one non-limitative embodiment of the invention, the movement of the interference phenomenon G on a sequence SQ of captured images can be tracked in order to assist the characterization of the nature of the phenomenon. In this way, in the event of an interference phenomenon G, such as fog, no movement will be detected on the sequence SQ of the captured images I, whereas in the case of an interference phenomenon such as water, movement will be detected. This process is based on the tracking of zones illuminated on the sequence SQ of images I. As this tracking process is already known to experts, it will not be described here.

This tracking process is especially useful for distinguishing between fog and water in cases where no spray of water is generated (for example, in cases of fine rain) or if the vehicle is travelling at low speeds. In this case, the captured image I presents a continuous homogenous zone.

In a fourth stage 4), once a visibility interference phenomenon G has been detected and its nature has been defined, an appropriate processing CD can be carried out in real time on the vehicle V.

In non-limitative examples, this can involve:
an automatic adaptation of the vehicle's V lighting system in relation to the indications on the nature of the interference phenomenon G by increasing the intensity of the fog lights. In addition, account can be taken of the presence of the obstacle O as indicated above; or
the sending of an alarm system to the driver of the vehicle V, so that he himself can adjust the intensity of his lights, for example by switching on or increasing the intensity of his fog lights; or
the automatic switching on of the vehicle's lights (in the example given, the rear signalling system, that is to say, the tail-lights and the fog lights).

It will be noted that this fourth stage is carried out as and when the video images are processed by the process described above. In this way, the appropriate processing CD, such as, for example, the automatic adaptation of the rear lights, is carried out in real time, since it is effected each time an interference phenomenon is detected, with a detection taking place with every capture of an image I.

Figure 6:
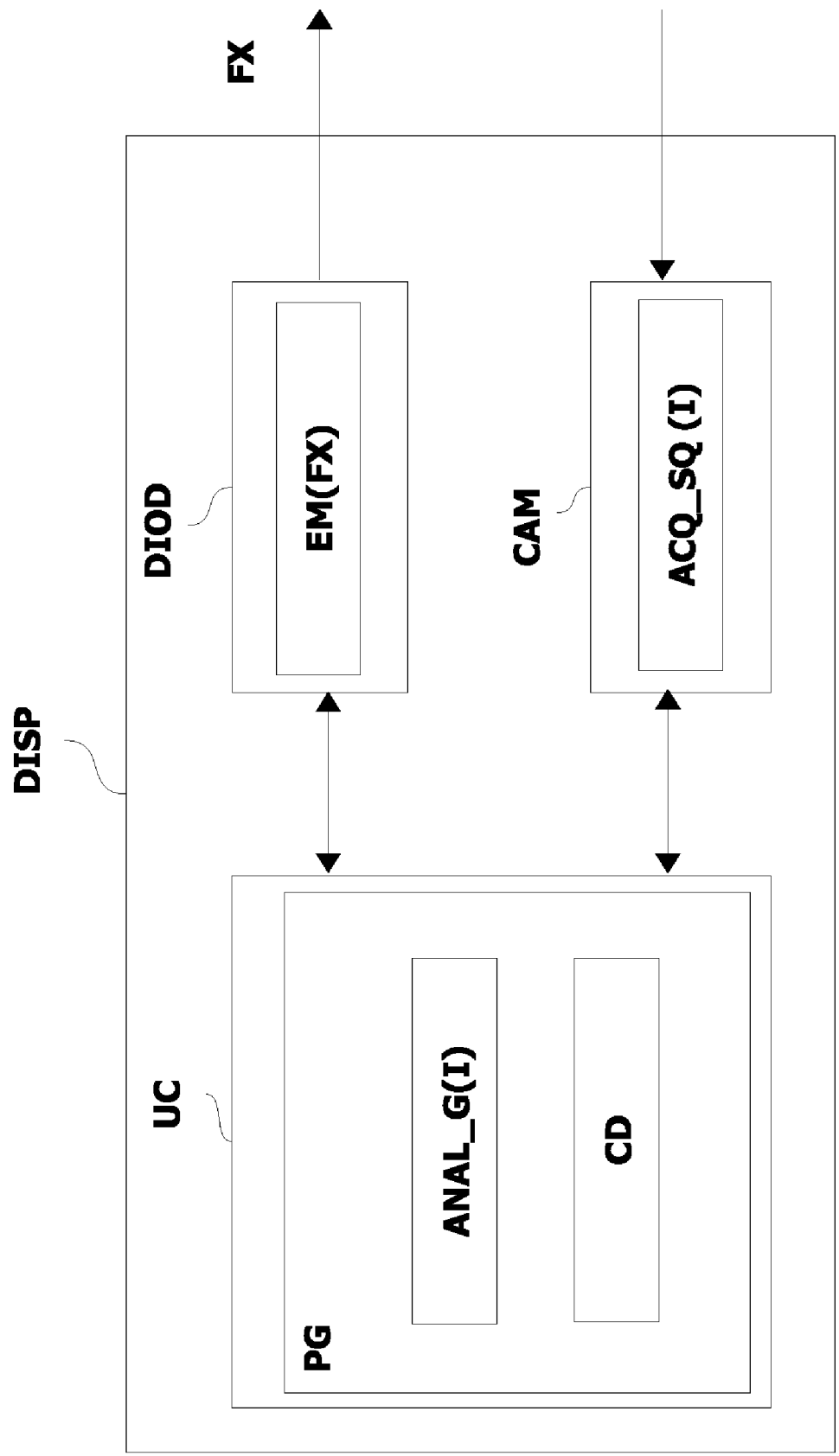
FIG. 6 is a proposed non-limitative embodiment of a detection device enabling the process described by FIG. 1 to be implemented.

The process according to the invention is implemented by a detection device DISP shown in FIG. 6.

This DISP device comprises:
a light source DIOD emitting a beam of light FX from a vehicle V, with this beam of light being emitted into the field of vision of a camera CAM of the vehicle V; and
a control unit UC to establish the presence and the nature of a visibility interference phenomenon G on the basis of at least one image captured by the camera CAM.

In addition, the control unit UC enables the light source DIOD and the camera CAM to be controlled and also ensures the control (automatic adaptation of the vehicle's lights, automatic switching of the vehicle's lights) of the operation of the appropriate processing CD stage.

In one non-limitative embodiment of the present invention, the detection device DISP can also include the video camera CAM enabling an image I to be captured a illustrated in FIG. 6. It will be noted that in this case the control unit UC can also be located in the video camera CAM.

The light source DIOD and the camera CAM are described in greater detail below.

The Light Source DIOD.

The light source DIOD is a diode of the LED type. In other non-limitative embodiments it may be a laser diode, OLED, a halogen lamp with a light concentrator etc. or any other source capable of emitting a beam that is compatible with the camera CAM, as will be seen below.

In one non-limitative example, it is placed inside the vehicle's lighting and signalling system (in the example used, a rear light of the vehicle V, because of the additional protection afforded by the glass light housing) or on the vehicle in the area of the lighting on the vehicle registration plate or on the lid of the rear hatch etc., all of these positions being ideally suited to detect the presence of an interference phenomenon G, generated for example by one of the rear wheels. In fact, in view of its size (in the range of a $cm^3$), a beam of light generator, comprising the infra-red light source DIOD, plus an optical projection system, is easy to incorporate into the lighting and signalling system of a vehicle—in the example given, for instance, in the rear light. Moreover, an electronic control system (steering the light source DIOD and the camera CAM) can be placed in the rear part of a light housing, which frequently has the necessary room.

The Camera CAM

This camera is, for example, of the type VGA with the definition 640*480 (in other words, a captured image I comprising 8 bits (per pixel) with 640 columns and 480 lines) and comprises a lens (not shown) for this purpose. The image I that is captured in this way is in full resolution.

In a non-limitative example, the video camera CAM will capture 10 images per second. It will be noted that a sequence of images SQ is made up of between twenty and a hundred or so images, depending on speed of travel of the vehicle V.

Evidently a different type of camera with a different resolution can be used.

It will be noted that the camera CAM being used to detect the presence of an interference phenomenon G must be sensitive to the wavelength used for the beam of light FX. Again, in a non-limitative example, cameras of the type CMOS or CCD may be used, as these are traditionally employed in motor vehicle applications because they are silicon based and have a response spectrum of between 400 nm and 1100 nm approximately (the wavelength range seen by the camera). This response spectrum is thus compatible with an infra-red beam of light FX. In this way, the beam of light FX will be seen by the camera CAM because it has a wavelength that lies within the range of wavelengths at which the camera CAM is sensitive.

Furthermore, the field of vision CAM_V of the camera CAM cuts the beam of light at a fairly short distance (between 1 and 5 meters) from the emission source DIOD of the beam of light FX. This enables precise information to be obtained on the interference phenomena G situated, in the example shown, at the rear of the vehicle, and is certain to detect the presence of such a phenomena and in particular a spray of water. Moreover, the range of the field of vision CAM_V of the camera is determined in such a way as to cover an area in which an interference phenomenon G (for example a spray of water) could be generated. In a non-limitative example, this is in the range of 20 meters.

It will be noted that all the stages of the process described above are effected for one or more (sequence SQ) captured images I by the video camera CAM—and this in real time. That is to say, that all the stages take no more than $\frac{1}{10}$ of a second in the example of a sequence of 10 images per second captured by the camera CAM.

It will also be noted that the implementation of the detection process described above can be carried out using a micro programmed software device, a cabled logical system or by hardware electronic components.

In this way, the detection device DISP can comprise a computer program product TG having one or more sequences of instructions that can be carried out by an information processing unit such as a microprocessor, the processing unit of a microcontroller, an ASIC or a computer etc., with the execution of the said sequences of instructions effecting the start-up of the process described.

A computer program PG of this type can be stored in a non-volatile memory of the ROM or EEPROM or FLASH type. The computer program can be stored in the memory at the works or loaded or remote loaded subsequently. The sequences of instructions can be sequences of machine instructions or again they may be sequences of a control language interpreted by the processing unit at the moment they are given.

In the non-limitative example in FIG. 6, the computer program PG is stored in the memory of the control unit UC of the device DISP.

Evidently, the description of the process is not limited to the embodiments described above. In this way, in another non-limitative embodiment, the beam of light FX that is emitted may be modulated. For example, it might be envisaged that the light is issued at every "n" images captured by the camera CAM and then comparisons or abstractions are made (simple image processing operations) between the images with and without modulated light. As a result of these comparisons/abstractions, it is simple to distinguish the beam of light FX in such a way as to study the interference phenomena G that become visible as described above. Insofar as "n" is high (for example displaying 29 images without modulated light and the 30th modulated in a system capturing 30 images/second) it is possible to superimpose the function "detection of interference phenomenon" onto another function such as a parking aid function, without changing the detection function of the interference phenomenon.

Evidently, what was described above for the example of a beam of light FX emitted in order to light up the rear of a motor vehicle V could also apply to a beam of light FX to light up the front of a motor vehicle V in order to detect a visibility interference phenomenon at the front of the vehicle. In this case, the vehicle V is fitted with a camera CAM positioned in the front.

In this case, after detecting a visibility interference phenomenon G at the front of the vehicle V, in non-limitative examples, the appropriate processing CD tracking the vehicle V in real time can be effect by:

automatically adapting the intensity of the front headlamps of the vehicle V in relation to the information provided on the nature of the interference phenomenon G by increasing the intensity of the headlamps (dipped or undipped) and/or by activating the fog lights. In addition, the presence of an obstacle O as indicated above will be taken into account; or automatically switching headlamps from their dipped to their undipped mode; or sending an alarm signal to the driver of the vehicle V so that he himself can increase the intensity of his headlamps if he can, for example, in order to switch on to increase the effect of his fog lights.

Furthermore, adjustments could be made to enable the appropriate processing CD also comprises a system whereby the detection information can be transmitted to other systems within the vehicle V, such as for example, a front camera that can track the white lines on the road. The camera could thus be warned that the road ahead is wet and if necessary, the intensity of the headlamps could be increased to ensure that the white lines in the road can be clearly perceived.

In this way, the present invention has the following advantages:

it can enable the presence of a spray of water to be detected, so that the rear lights can be appropriately adapted;

it can enable the nature of an interference phenomenon to be determined. In this way, in the event of fog, the foglights are switched on, whereas in the event of a spray of water, the intensity of the rear lights can be adjusted;

it enables a visibility interference phenomenon, which could be generated by the rear wheels of a vehicle, such as a spray of water, to be detected. It can also distinguish between a spray of water (a phenomenon generated by the vehicle itself) and fog (a phenomenon not generated by the vehicle);

it enables the presence of an obstacle such as a following vehicle to be detected and also its nature:

in the event that there is no such obstacle, the level of the rear lights is increased (if an interference phenomenon is detected);

in the event that an obstacle is detected, the level of intensity of the lights is increased in such a way that the driver of the following vehicle is not dazzled or prevented from seeing the vehicle in front of him. This also has the effect of consuming less and thereby saving energy;

it ensures that there is no confusion between an interference phenomenon and an obstacle, such as a following vehicle;

it prevents two cameras having to be used, one for the detection of an interference phenomenon and another for use as a parking aid. In this way, two functions can be carried out by the same camera, which is multi-functional. The invention is economical, because the additional cost of the function for the detection of an interference phenomenon is limited to the generation of the beam of light and the processing of the images with this latter being able to use the same hardware support as the parking aid; and it can be easily integrated into a lighting and signalling system, such as a sidelight or a headlamp (generator of light, camera) without having any means of installation impinging on the bodywork of the vehicle.

While the forms of apparatus herein described constitutes preferred embodiments of this invention, it is to be understood that the invention is not limited to these precise forms of apparatus, and that changes may be made therein without departing from the scope of the invention which is defined in the appended claims.

What is claimed is:

1. A process for the detection of a visibility interference phenomenon comprising the following steps:

emission of a beam of light from a vehicle, said beam of light being emitted into a field of vision of a camera of the vehicle; and determining the presence and the nature of the visibility interference phenomenon on the basis of at least one image of said beam of light captured by the camera; and wherein the determination of the nature of the visibility interference phenomenon is effected on the basis of a homogeneity of said visibility interference phenomenon on the image;

said visibility interference phenomenon and said determining step being effected by using said at least one image of said beam of light that is emitted into said field of said camera.

2. The process according to claim 1, wherein the determination of the nature of the said visibility interference phenomenon is effected on the basis of a homogeneity and a granulometry of the visibility interference phenomenon on said at least one image.

3. A process for the detection of a visibility interference phenomenon comprising the following steps:

emission of a beam of light from a vehicle, said beam of light being emitted into a field of vision of a camera of the vehicle; and determining the presence and the nature of a visibility interference phenomenon on the basis of at least one image captured by the camera;

wherein the determination of the nature of the visibility interference phenomenon is effected on the basis of a homogeneity of said visibility interference phenomenon on the image;

wherein the determination of the nature of the visibility interference phenomenon is effected on the basis of a tracking movement of the said visibility interference phenomenon.

4. The process according to claim 1, wherein the beam of light is modulated.

5. A detection device for a visibility interference phenomenon comprising:

a light source emitting a beam of light from a vehicle, with this beam of light being emitted within the field of vision of a camera of the vehicle; and a control unit to determine a presence and a nature of the visibility interference phenomenon on the basis of at least one image captured by the camera;

wherein said control unit determines said nature of the visibility interference phenomenon on the basis of the homogeneity of the visibility interference phenomenon on the image;

said control unit determining said visibility interference phenomenon by using said at least one image of said beam of light that is emitted into said field of said camera.

6. The process according to claim 5, wherein said process is performed using a detection device comprising a computer program product comprising one or more sequences of instructions that can be carried out by an information processing unit, the carrying out of the said one or more sequences of instructions being wherein the computer program enables the process of:

emission of said beam of light from the vehicle, said beam of light being emitted into said field of vision of said camera of the vehicle; and determining the presence and the nature of said visibility interference phenomenon on the basis of said at least one image captured by the camera;

wherein the determination of the nature of the visibility interference phenomenon is effected on the basis of said homogeneity of said visibility interference phenomenon.

7. A process for the detection of a visibility interference phenomenon comprising the following steps:

emission of a beam of light from a vehicle, said beam of light being emitted into a field of vision of a camera of the vehicle; and determining the presence and the nature of a visibility interference phenomenon on the basis of at least one image captured by the camera;

wherein the determination of the nature of the visibility interference phenomenon is effected on the basis of a homogeneity of said visibility interference phenomenon on said at least one image;

wherein the determination of the nature of the said visibility interference phenomenon is effected on the basis of the homogeneity and the granulometry of the visibility interference phenomenon on said at least one image;

wherein the determination of the nature of the visibility interference phenomenon is effected on the basis of a tracking movement of the said visibility interference phenomenon.

8. A detection device comprising:

at least one camera mounted on a rear of a vehicle;

a control coupled to said at least one camera for capturing an image behind the vehicle;

said control being adapted to determine the presence of at least one of rain or an obstacle in response to the homogeneity of the visibility interference phenomenon;

said control determining said visibility interference phenomenon by using said at least one image of said beam of light that is emitted into said field of said at least one camera.

9. The detection device according to claim 8, wherein said computer program bases the homogeneity of the visibility interference and granulometry of diffused light.

10. The detection device according to claim 8, wherein said computer program further comprises a diode light source coupled to a control, said diode light source generating a light beam that is compatible with said camera.

11. The detection device according to claim 10, wherein said diode light source generates said light beam when rear lights on said vehicle come on.

12. A process for the detection of a visibility interference phenomenon comprising the following steps:

emission of a beam of light from a vehicle, said beam of light being emitted into a field of vision of a camera of the vehicle; and determining the presence and the nature of a visibility interference phenomenon on the basis of at least one image captured by the camera;

wherein the determination of the nature of the visibility interference phenomenon is effected on the basis of a homogeneity of said visibility interference phenomenon on said at least one image whenever rear lights on said vehicle are on;

wherein the determination of the nature of the visibility interference phenomenon is effected on the basis of a tracking movement of the said visibility interference phenomenon.

13. The process according to claim 12, wherein said process further comprises the step of adjusting an intensity of rear lights on said vehicle in response to a detection of an obstacle.

* * * * *